(12) United States Patent
Tsuda et al.

(10) Patent No.: US 12,292,400 B2
(45) Date of Patent: May 6, 2025

(54) NON-INVASIVE SUBSTANCE ANALYSIS APPARATUS

(71) Applicant: Mitsubishi Electric Corporation, Tokyo (JP)

(72) Inventors: Yuki Tsuda, Tokyo (JP); Shusaku Hayashi, Tokyo (JP); Koichi Akiyama, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 18/834,630

(22) PCT Filed: Feb. 17, 2022

(86) PCT No.: PCT/JP2022/006342
§ 371 (c)(1),
(2) Date: Jul. 31, 2024

(87) PCT Pub. No.: WO2023/157164
PCT Pub. Date: Aug. 24, 2023

(65) Prior Publication Data
US 2024/0418663 A1 Dec. 19, 2024

(51) Int. Cl.
*G01N 25/20* (2006.01)
(52) U.S. Cl.
CPC ................ *G01N 25/20* (2013.01)
(58) Field of Classification Search
CPC ..................................... G01N 25/20
See application file for complete search history.

(56) References Cited

U.S. PATENT DOCUMENTS

| 7,667,200 B1* | 2/2010 | Watts ............... | G01J 5/08 |
| | | | 250/338.1 |
| 7,820,970 B1* | 10/2010 | Shaw ............... | G01J 5/44 |
| | | | 250/338.1 |
| 2017/0146455 A1 | 5/2017 | Mäntele et al. | |
| 2018/0000386 A1 | 1/2018 | Yamakawa | |

(Continued)

FOREIGN PATENT DOCUMENTS

| JP | 2008-232893 A | 10/2008 |
| JP | 2017-519214 A | 7/2017 |

(Continued)

OTHER PUBLICATIONS

International Search Report and Written Opinion mailed on Apr. 12, 2022, received for PCT Application No. PCT/JP2022/006342, filed on Feb. 17, 2022, 12 pages including English Translation.

(Continued)

*Primary Examiner* — Mirellys Jagan
(74) *Attorney, Agent, or Firm* — XSENSUS LLP

(57) ABSTRACT

A non-invasive substance analysis apparatus includes: a sample support plate; an excitation light source; and a temperature sensor. The sample support plate has a main surface including a sample placement region, and a main surface opposite to the main surface. The temperature sensor is provided on the main surface. A through hole extending from the sample placement region to the main surface is provided in the sample support plate. Excitation light emitted from the excitation light source is applied to a sample placed on the sample placement region through the through hole.

9 Claims, 9 Drawing Sheets

(56) References Cited

U.S. PATENT DOCUMENTS

| | | | |
|---|---|---|---|
| 2018/0328835 A1 | 11/2018 | Bauer et al. | |
| 2019/0302019 A1 | 10/2019 | Bauer et al. | |
| 2021/0356322 A1* | 11/2021 | Nam | G01J 3/0297 |
| 2021/0401291 A1 | 12/2021 | Schriek et al. | |
| 2022/0404275 A1 | 12/2022 | Hayashi et al. | |
| 2023/0053065 A1 | 2/2023 | Tsuda et al. | |
| 2024/0089568 A1* | 3/2024 | Sofronov | H04N 23/11 |

FOREIGN PATENT DOCUMENTS

| | | | |
|---|---|---|---|
| JP | 2019-507319 A | 3/2019 | |
| JP | 2019-507320 A | 3/2019 | |
| JP | 2020-154105 A | 9/2020 | |
| JP | 6786027 B1 | 11/2020 | |
| WO | WO-2007074422 A2 * | 7/2007 | A61B 5/0095 |
| WO | 2016/117520 A1 | 7/2016 | |
| WO | 2021/131126 A1 | 7/2021 | |
| WO | 2021/176583 A1 | 9/2021 | |
| WO | WO-2023157163 A1 * | 8/2023 | |

OTHER PUBLICATIONS

Notice of Reasons for Refusal mailed on Aug. 30, 2022, received for JP Application 2022-542213, 9 pages including English Translation.

Decision to Grant mailed on Dec. 6, 2022, received for JP Application 2022-542213, 6 pages including English Translation.

* cited by examiner

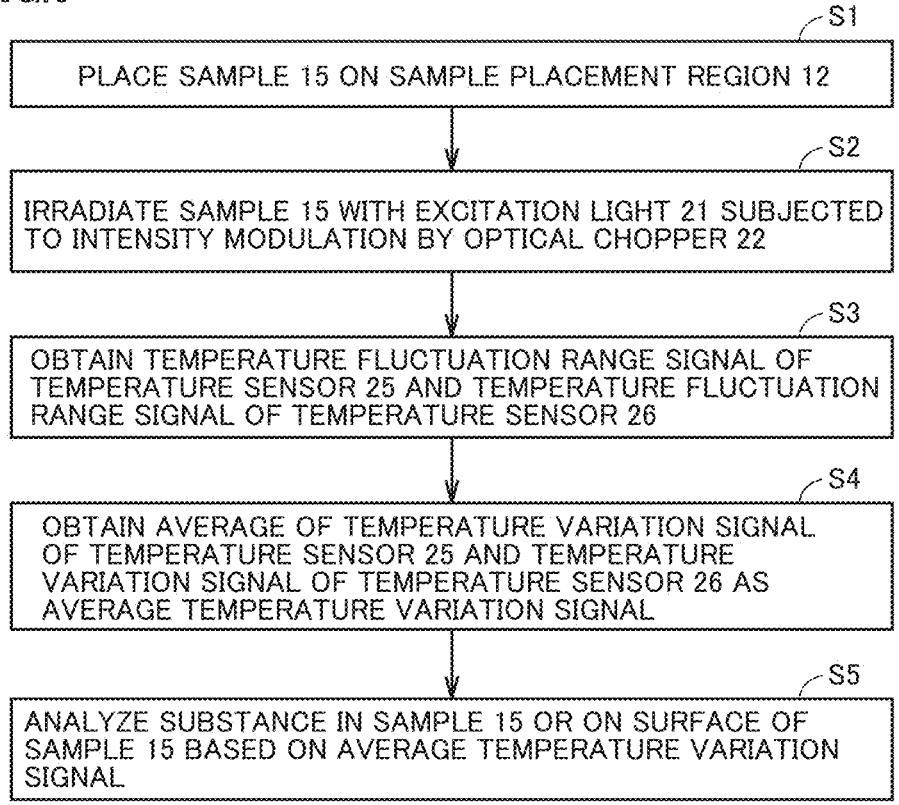
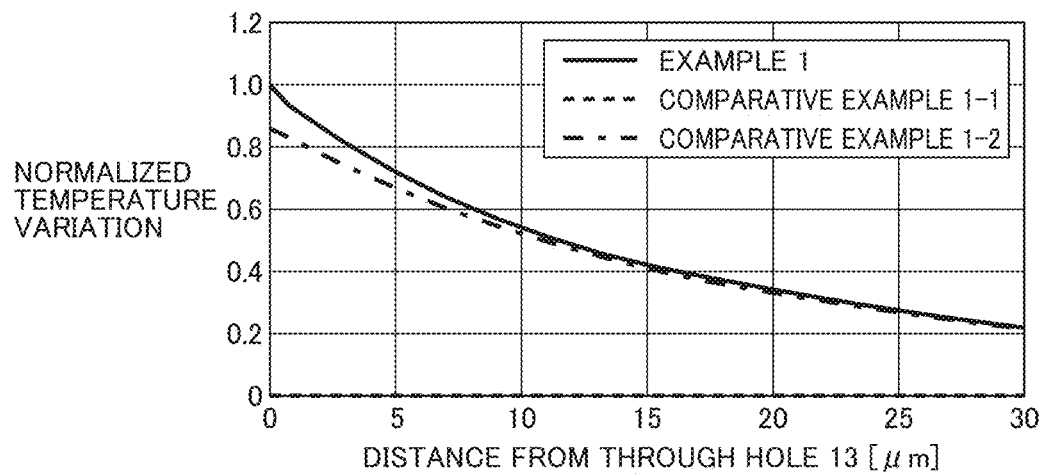

NON-INVASIVE SUBSTANCE ANALYSIS APPARATUS

CROSS-REFERENCE TO RELATED APPLICATION

This application is a national stage application, pursuant to 35 U.S.C. § 371, of International Patent Application No. PCT/JP2022/006342, filed Feb. 17, 2022, the entire contents of which are incorporated herein by reference.

TECHNICAL FIELD

The present disclosure relates to a non-invasive substance analysis apparatus.

BACKGROUND ART

Japanese National Patent Publication No. 2017-519214 (PTL 1) discloses a non-invasive analysis system including an optical medium, an infrared light source, a probe light source, and a photodiode. Specifically, a biological sample is placed on the optical medium. The infrared light source emits infrared light. The infrared light is applied to the biological sample through the optical medium. The infrared light is absorbed by the biological sample, which causes the biological sample to generate heat. A degree of absorption heat of the biological sample depends on an amount or concentration of a biological component in the sample or on a surface of the sample.

The probe light source emits probe light, which is visible light, toward the optical medium. The probe light is totally internally reflected at an interface between the optical medium and the biological sample, and exits from the optical medium. The absorption heat of the biological sample is transferred to the optical medium to change a refractive index of the optical medium. The change in refractive index of the optical medium affects the total internal reflection of the probe light at the interface between the optical medium and the biological sample, which causes a change in traveling direction of the probe light exiting from the optical medium. The photodiode functions as an optical position sensor to detect the change in traveling direction of the probe light. The amount or concentration of the biological component is measured from the change in traveling direction of the probe light detected by the photodiode. For example, when the sample is a skin of a patient, a blood glucose level of the patient is measured as the biological component.

CITATION LIST

Patent Literature

PTL 1: Japanese National Patent Publication No. 2017-519214

SUMMARY OF INVENTION

Technical Problem

However, in the non-invasive analysis system disclosed in PTL 1, the absorption heat of the biological sample quickly diffuses throughout the optical medium. Therefore, the change in traveling direction of the probe light caused by the absorption heat of the biological sample is small, and thus, the biological component in the sample or on the surface of the sample cannot be analyzed accurately. The present disclosure has been made in view of the above-described problem, and an object thereof is to provide a non-invasive substance analysis apparatus capable of more accurately analyzing a substance in a sample or on a surface of the sample.

Solution to Problem

A non-invasive substance analysis apparatus according to the present disclosure includes: a sample support plate; an excitation light source; and a temperature sensor. The sample support plate has a first main surface including a sample placement region, and a second main surface opposite to the first main surface. The excitation light source emits excitation light toward a sample placed on the sample placement region. The temperature sensor is provided on the first main surface. A through hole extending from the sample placement region to the second main surface is provided in the sample support plate. The excitation light is applied to the sample through the through hole.

Advantageous Effects of Invention

In the non-invasive substance analysis apparatus according to the present disclosure, the through hole through which the excitation light passes is provided in the sample support plate. Therefore, the excitation light reaches the sample at a stronger light intensity, without being absorbed by the sample support plate. The absorption heat of the sample increases. In addition, the absorption heat of the sample becomes less likely to escape in a thickness direction (a direction in which the first main surface and the second main surface face each other) of the sample support plate. A temperature signal output from the temperature sensor during irradiation of the sample with the excitation light increases. Therefore, a substance in the sample or on a surface of the sample can be analyzed more accurately.

BRIEF DESCRIPTION OF DRAWINGS

FIG. 5 is a diagram showing a flowchart of a non-invasive substance analysis method according to the first embodiment.

FIG. 6 is a diagram showing simulation results of normalized temperature variations in Example 1 and Comparative Examples 1-1 and 1-2.

DESCRIPTION OF EMBODIMENTS

Figure 1:
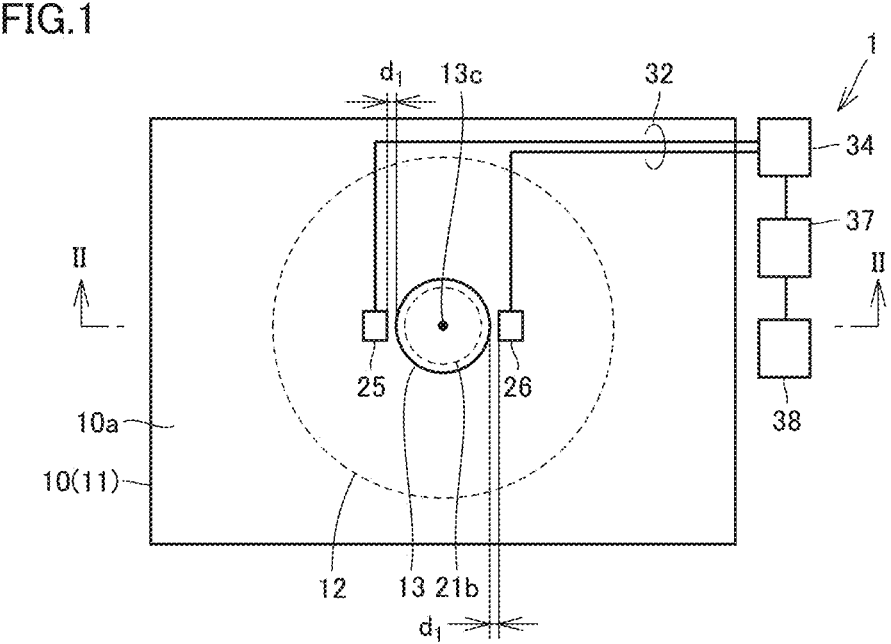
FIG. 1 is a schematic plan view of a non-invasive substance analysis apparatus according to a first embodiment.

Embodiments will be described below. The same configurations are denoted by the same reference numerals and description thereof will not be repeated.

First Embodiment

Figure 2:
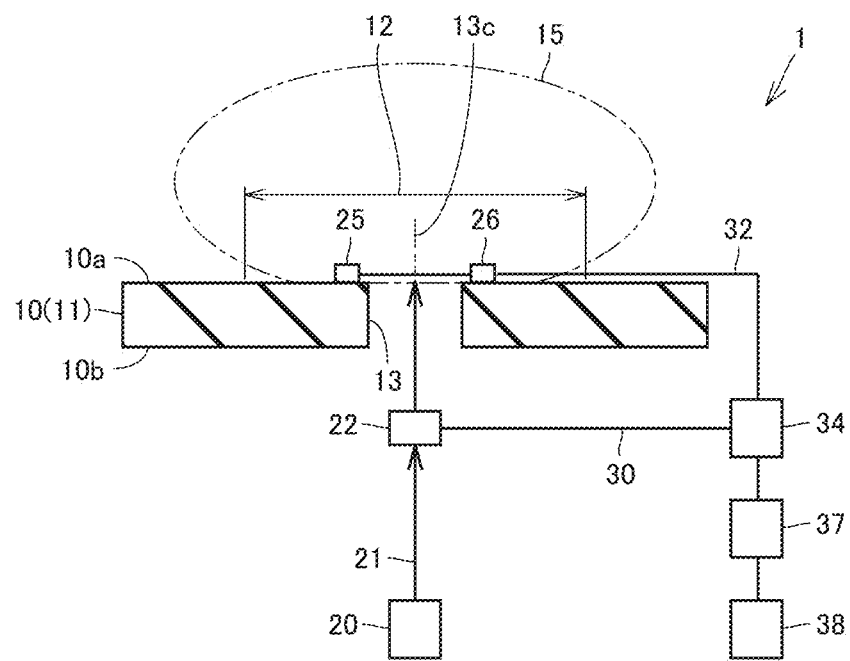
FIG. 2 is a schematic cross-sectional view of the non-invasive substance analysis apparatus according to the first embodiment taken along a cross-sectional line II-II shown in FIG. 1.

A non-invasive substance analysis apparatus 1 according to a first embodiment will be described with reference to FIGS. 1 to 4. Referring to FIGS. 1 and 2, non-invasive substance analysis apparatus 1 includes a sample support plate 10, an excitation light source 20, an optical chopper 22, temperature sensors 25 and 26, a lock-in amplifier 34, a signal processing unit 37, and a substance analysis unit 38.

Sample support plate 10 has a main surface 10a, and a main surface 10b opposite to main surface 10a. Main surface 10a includes a sample placement region 12 on which sample 15 is placed. Sample 15 is a biological sample such as, for example, a finger, a wrist, an arm, an earlobe, or a lip of a patient. In the present embodiment, sample support plate 10 is formed by a substrate 11. Substrate 11 is made of a material that is opaque to excitation light 21. Substrate 11 is made of, for example, plastic such as polyethylene, polycarbonate, polyurethane, or acrylic resin, or glass.

A through hole 13 extending from sample placement region 12 to main surface 10b is provided in sample support plate 10. A size of sample 15 is larger than a size of through hole 13 in a plan view of main surface 10a.

Excitation light source 20 emits excitation light 21 toward sample 15 placed on sample placement region 12. A wavelength of excitation light 21 is determined in accordance with an absorption wavelength of a substance in sample 15 or on a surface of sample 15. Excitation light 21 is, for example, mid-infrared light. The wavelength of excitation light 21 is, for example, equal to or more than 6.0 μm. The wavelength of excitation light 21 may be equal to or more than 8.0 μm. The wavelength of excitation light 21 is, for example, equal to or less than 13.0 μm. The wavelength of excitation light 21 may be equal to or less than 11.0 μm. Excitation light 21 may be light having a plurality of wavelengths. For example, when non-invasive substance analysis apparatus 1 is used to measure a blood glucose level of the patient, a wavelength range of excitation light 21 is a wavelength range including a wavelength of a fingerprint spectrum of glucose (e.g., a wavelength range of equal to or more than 8.5 μm and equal to or less than 10 μm). Excitation light source 20 is, for example, a quantum cascade laser that can emit broadband mid-infrared light. Sample 15 may be irradiated with reference light that is not absorbed by the substance in sample 15 or on the surface of sample 15, together with excitation light 21.

Optical chopper 22 subjects excitation light 21 to periodical intensity modulation. Optical chopper 22 includes a plurality of rotating blades, for example. The plurality of rotating blades are made of a material that is opaque to excitation light 21. When excitation light 21 is blocked by one of the plurality of rotating blades, sample 15 is not irradiated with excitation light 21. In contrast, when excitation light 21 passes through a space between a pair of rotating blades adjacent to each other, of the plurality of rotating blades, sample 15 is irradiated with excitation light 21. In this way, optical chopper 22 subjects excitation light 21 emitted from excitation light source 20 to intensity modulation. Optical chopper 22 transmits, to lock-in amplifier 34 through an electrical wire 30, a reference signal having the same frequency as an intensity modulation frequency of excitation light 21 subjected to intensity modulation.

Excitation light 21 subjected to intensity modulation by optical chopper 22 enters sample support plate 10 from the main surface 10b side. Excitation light 21 is applied to sample 15 through through hole 13. Excitation light 21 travels on a central axis 13c of through hole 13, for example. When excitation light 21 passes through optical chopper 22, sample 15 is irradiated with excitation light 21. Excitation light 21 is absorbed by the substance in sample 15 or on the surface of sample 15. The absorption of excitation light 21 by the substance in sample 15 or on the surface of sample 15 causes sample 15 to generate absorption heat. In contrast, when excitation light 21 is blocked by optical chopper 22, sample 15 is not irradiated with excitation light 21 and sample 15 does not generate the absorption heat. Therefore, a temperature of sample 15 varies in accordance with the intensity modulation frequency of excitation light 21.

The substance in sample 15 or on the surface of sample 15 is, for example, a biological component. When non-invasive substance analysis apparatus 1 is used to obtain the blood glucose level of the patient, the substance analyzed by non-invasive substance analysis apparatus 1 is glucose present in an interstitial fluid in epidermis of the patient.

Each of temperature sensors 25 and 26 is provided on main surface 10a. Each of temperature sensors 25 and 26 is provided in sample placement region 12. When sample 15 is placed on sample placement region 12, each of temperature sensors 25 and 26 comes into contact with sample 15 to detect the temperature of sample 15. Each of temperature sensors 25 and 26 detects the temperature of sample 15 and outputs a temperature signal corresponding to the temperature to lock-in amplifier 34. Specifically, temperature sensor 25 detects a temperature of a portion of sample 15 with which temperature sensor 25 is in contact, and outputs a temperature signal corresponding to the temperature to lock-in amplifier 34. Temperature sensor 26 detects a temperature of a portion of sample 15 with which temperature sensor 26 is in contact, and outputs a temperature signal corresponding to the temperature to lock-in amplifier 34.

Since the temperature of sample 15 varies in accordance with the intensity modulation frequency of excitation light 21, the temperature signal output from each of temperature sensors 25 and 26 also varies in accordance with the intensity modulation frequency of excitation light 21. For example, each of temperature sensors 25 and 26 outputs a minimum value of the temperature signal when sample 15 is not irradiated with excitation light 21, and outputs a maximum value of the temperature signal when sample 15 is irradiated with excitation light 21. A difference between the maximum value and the minimum value of the temperature signal is an amplitude of the temperature signal. The amplitude of the temperature signal of each of temperature sensors 25 and 26 corresponds to a temperature variation of sample 15 measured by each of temperature sensors 25 and 26 during analysis of sample 15. In the present embodiment, "during analysis of sample 15" refers to a time period during which sample 15 is irradiated with excitation light 21 subjected to intensity modulation.

Temperature sensors 25 and 26 are disposed near through hole 13. A distance $d_1$ between each of temperature sensors 25 and 26 and through hole 13 is, for example, equal to or less than 50 μm. Distance $d_1$ may be equal to or less than 20 μm, or may be equal to or less than 10 μm. Distance $d_1$ is equal to or less than 10% of the size of through hole 13 (e.g., a diameter of through hole 13). Distance $d_1$ may be equal to or less than 5% of the size of through hole 13. Temperature sensors 25 and 26 are disposed to be rotationally symmetrical with respect to central axis 13c of through hole 13 in a plan view of main surface 10a.

Figure 3:
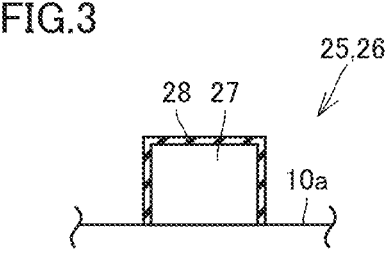
FIG. 3 is a schematic partially enlarged cross-sectional view of the non-invasive substance analysis apparatus according to the first embodiment.

Referring to FIG. 3, each of temperature sensors 25 and 26 includes a temperature sensor main body 27. Each of temperature sensors 25 and 26 may further include a protective film 28.

Temperature sensor main body 27 is, for example, a thermocouple, a thermopile, a thermistor, or a diode.

In the thermocouple, two dissimilar material pieces are brought into contact with each other and the temperature of sample 15 is measured from the thermoelectromotive force generated at a contact portion of the two dissimilar material pieces. Each of the two material pieces that form the thermocouple is made of, for example, iron, a copper-nickel alloy, copper, a nickel-chromium alloy, a nickel-aluminum alloy, a nickel-silicon alloy, a nickel chromium silicon alloy, platinum, a platinum-rhodium alloy, bismuth, antimony, or a combination thereof. Each of the two material pieces that form the thermocouple may be made of p-type polysilicon and n-type polysilicon. The thermopile is formed by connecting a plurality of thermocouples.

An electrical resistance of the thermistor changes in accordance with a temperature of the thermistor. The temperature of sample 15 is detected from the electrical resistance of the thermistor. The thermistor is preferably made of a material having a large temperature resistance coefficient. The thermistor is made of, for example, vanadium oxide, NiMoCo oxide, Ti, polycrystalline silicon, amorphous silicon, amorphous silicon germanium, $MnO_3$, or YBaCuO.

A forward voltage of the diode changes in accordance with a temperature of the diode. The temperature of sample 15 is detected from the forward voltage of the diode. The diode is, for example, an Si diode.

Protective film 28 covers temperature sensor main body 27. Protective film 28 prevents sample 15 from coming into contact with temperature sensor main body 27. It is desirable that protective film 28 should have a low thermal conductivity (e.g., a thermal conductivity of 0.5 W/(m•K) or less) and a small thickness (e.g., a thickness of 10 μm or less). Since the thermal conductivity of protective film 28 is low, the absorption heat of sample 15 is less likely to quickly diffuse throughout sample support plate 10. Since protective film 28 is thin, the absorption heat of sample 15 is efficiently conducted to temperature sensor main body 27, even when the thermal conductivity of protective film 28 is low.

Referring to FIG. 2, lock-in amplifier 34 is connected to optical chopper 22 by electrical wire 30. Lock-in amplifier 34 receives, from optical chopper 22, the reference signal having the same frequency as the intensity modulation frequency of excitation light 21 subjected to intensity modulation. Referring to FIGS. 1 and 2, lock-in amplifier 34 is connected to each of temperature sensors 25 and 26 by an electrical wire 32. Lock-in amplifier 34 receives the temperature signal corresponding to the temperature of sample 15 from each of temperature sensors 25 and 26. Specifically, lock-in amplifier 34 receives, from temperature sensor 25, the temperature signal corresponding to the temperature of the portion of sample 15 with which temperature sensor 25 is in contact. Lock-in amplifier 34 receives, from temperature sensor 26, the temperature signal corresponding to the temperature of the portion of sample 15 with which temperature sensor 26 is in contact.

Lock-in amplifier 34 performs synchronous detection of the temperature signal received from each of temperature sensors 25 and 26 with the reference signal received from optical chopper 22. In this way, lock-in amplifier 34 outputs a temperature variation signal of temperature sensor 25 and a temperature variation signal of temperature sensor 26. The temperature variation signal of temperature sensor 25 is a temperature variation signal corresponding to the temperature variation of sample 15 measured by temperature sensor 25 during analysis of sample 15. The temperature variation signal of temperature sensor 26 is a temperature variation signal corresponding to the temperature variation of sample 15 measured by temperature sensor 26 during analysis of sample 15.

Figure 4:
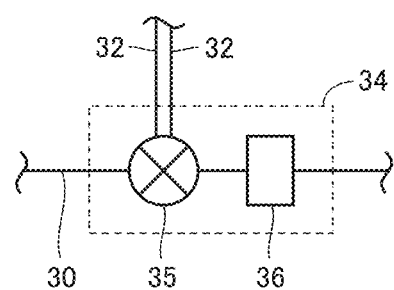
FIG. 4 is a circuit diagram of a lock-in amplifier.

The operation of lock-in amplifier 34 will be specifically described with reference to FIG. 4. Lock-in amplifier 34 includes a multiplier 35 and a low pass filter 36. Multiplier 35 multiplies the temperature signal of temperature sensor 25 and the reference signal. Multiplier 35 outputs a DC component proportional to the amplitude of the temperature signal of temperature sensor 25, and an AC component that varies at a frequency that is twice as high as the intensity modulation frequency of excitation light 21. Low pass filter 36 removes the AC component and allows the DC component to pass therethrough. In this way, lock-in amplifier 34 outputs the DC component proportional to the amplitude of the temperature signal of temperature sensor 25. The amplitude of the temperature signal of temperature sensor 25 corresponds to the temperature variation of the portion of sample 15 with which temperature sensor 25 is in contact during analysis of sample 15. Therefore, the DC component is the temperature variation signal of temperature sensor 25.

Similarly, lock-in amplifier 34 outputs a DC component proportional to the amplitude of the temperature signal of temperature sensor 26. The DC component is the temperature variation signal of temperature sensor 26.

Referring to FIGS. 1 and 2, signal processing unit 37 is connected to lock-in amplifier 34. Signal processing unit 37 receives the temperature variation signal of temperature sensor 25 and the temperature variation signal of temperature sensor 26 from lock-in amplifier 34. Signal processing unit 37 calculates an average of the temperature variation signal of temperature sensor 25 and the temperature variation signal of temperature sensor 26. Signal processing unit 37 outputs an average temperature variation signal corresponding to the average of the temperature variation signal of temperature sensor 25 and the temperature variation signal of temperature sensor 26. Signal processing unit 37 is, for example, a microcomputer including a processor and a storage device. The processor executes a program stored in the storage device, whereby signal processing unit 37 operates.

Substance analysis unit 38 is connected to signal processing unit 37. Substance analysis unit 38 receives the average temperature variation signal from signal processing unit 37. Substance analysis unit 38 analyzes the substance in sample 15 or on the surface of sample 15 based on the average temperature variation signal.

For example, substance analysis unit 38 specifies the type of the substance in sample 15 or on the surface of sample 15 and calculates an amount or concentration of the substance, by referring to a data table in which the wavelength of excitation light 21 and the type of the substance are associated with each other and a data table in which the magnitude of the average temperature variation signal and the amount or concentration of the substance are associated with each other. Substance analysis unit 38 is, for example, a microcomputer including a processor and a storage device. These data tables are stored in the storage device. The processor executes a program stored in the storage device, whereby substance analysis unit 38 operates.

A thermal conductivity of substrate 11 may be equal to or less than 5 W/(m•K), may be equal to or less than 2 W/(m•K), may be equal to or less than 1 W/(m•K), or may be equal to or less than 0.3 W/(m•K), for example. Therefore, the absorption heat generated in sample 15 by irradiation of sample 15 with excitation light 21 becomes less likely to quickly diffuse throughout substrate 11, and the temperature variation signal of each of temperature sensors 25 and 26 increases. The substance in sample 15 or on the surface of sample 15 can be analyzed with a higher degree of accuracy.

It is preferable that the thermal conductivity of substrate 11 should be lower than a thermal conductivity of sample 15. For example, when sample 15 is a human skin, the thermal conductivity of sample 15 is about 0.5 W/(m•K). When substrate 11 is made of plastic, the thermal conductivity of substrate 11 is equal to or more than 0.1 W/(m•K) and equal to or less than 0.3 W/(m•K). Therefore, the absorption heat generated in sample 15 by irradiation of sample 15 with excitation light 21 becomes less likely to quickly diffuse throughout substrate 11, and the temperature variation signal of each of temperature sensors 25 and 26 increases. The substance in sample 15 or on the surface of sample 15 can be analyzed with a higher degree of accuracy.

A thermal diffusion length L of the absorption heat of sample 15 is given by the following Expression (1):

$$L = \sqrt{\frac{\alpha}{\pi f}} \quad (1)$$

where f represents a frequency of the absorption heat of sample 15 (intensity modulation frequency of excitation light 21), and a represents a thermal diffusion coefficient of sample 15.

In light of Expression (1) above, the frequency of the absorption heat of sample 15 (intensity modulation frequency of excitation light 21) is set to be, for example, equal to or more than 5 Hz and equal to or less than 100 Hz, in order to analyze the substance (e.g., glucose in an interstitial fluid) present in sample 15 that is distant by several tens of micrometers or more from the surface of sample 15.

A non-invasive substance analysis method according to the present embodiment using non-invasive substance analysis apparatus 1 will be described with reference to mainly FIG. 5.

The non-invasive substance analysis method according to the present embodiment includes placing sample 15 on sample placement region 12 (S1). When there is a difference between the temperature of sample support plate 10 and the temperature of sample 15, the heat moves between sample support plate 10 and sample 15. This movement of the heat makes detection of the temperature variation signals difficult, and thus, makes analysis of the substance in sample 15 or on the surface of sample 15 difficult. Thus, step S2 described below is not performed until a thermal equilibrium state is achieved between sample support plate 10 and sample 15. The achievement of the thermal equilibrium state between sample support plate 10 and sample 15 can be detected by temperature sensors 25 and 26. For example, when a change in temperature signals of temperature sensors 25 and 26 per unit time becomes equal to or less than a threshold value (e.g., 0.1° C./min), it is determined that the thermal equilibrium state is achieved between sample support plate 10 and sample 15, and step S2 is performed.

The non-invasive substance analysis method according to the present embodiment includes irradiating sample 15 with excitation light 21 subjected to intensity modulation by optical chopper 22 (S2). Optical chopper 22 transmits the reference signal having the same frequency as the intensity modulation frequency of excitation light 21 to lock-in amplifier 34 through electrical wire 30.

When excitation light 21 passes through optical chopper 22, excitation light 21 is absorbed by the substance in sample 15 or on the surface of sample 15, which causes sample 15 to generate the absorption heat. In contrast, when excitation light 21 is blocked by optical chopper 22, sample 15 does not generate the absorption heat. Therefore, the temperature signals output from temperature sensors 25 and 26 vary in accordance with the intensity modulation frequency of excitation light 21.

The non-invasive substance analysis method according to the present embodiment includes obtaining the temperature variation signal of temperature sensor 25 and the temperature variation signal of temperature sensor 26 (S3).

Specifically, lock-in amplifier 34 receives the reference signal from optical chopper 22 and receives the temperature signal from temperature sensor 25. Lock-in amplifier 34 includes multiplier 35 and low pass filter 36. Multiplier 35 multiplies the temperature signal of temperature sensor 25 and the reference signal. Multiplier 35 outputs the DC component proportional to the amplitude of the temperature signal of temperature sensor 25, and the AC component that varies at a frequency that is twice as high as the intensity modulation frequency of excitation light 21. Low pass filter 36 removes the AC component and allows the DC component to pass therethrough. In this way, lock-in amplifier 34 outputs the DC component proportional to the amplitude of the temperature signal of temperature sensor 25. The DC component is the temperature variation signal of temperature sensor 25.

Similarly, lock-in amplifier 34 outputs the DC component proportional to the amplitude of the temperature signal of temperature sensor 26. The DC component is the temperature variation signal of temperature sensor 26.

The non-invasive substance analysis method according to the present embodiment includes obtaining the average of the temperature variation signal of temperature sensor 25 and the temperature variation signal of temperature sensor 26 as the average temperature variation signal (S4). Specifically, signal processing unit 37 receives the temperature variation signal of temperature sensor 25 and the temperature variation signal of temperature sensor 26 from lock-in amplifier 34. Signal processing unit 37 calculates the average of the temperature variation signal of temperature sensor 25 and the temperature variation signal of temperature sensor 26 as the average temperature variation signal. Signal processing unit 37 outputs the average temperature variation signal to substance analysis unit 38.

The non-invasive substance analysis method according to the present embodiment includes analyzing the substance in sample 15 or on the surface of sample 15 based on the average temperature variation signal (S5). Substance analysis unit 38 receives the average temperature variation signal from signal processing unit 37. For example, substance analysis unit 38 specifies the type of the substance in sample 15 or on the surface of sample 15 and calculates the amount or concentration of the substance, by referring to the data table in which the wavelength of excitation light 21 and the type of the substance are associated with each other and the data table in which the magnitude of the average temperature variation signal and the amount or concentration of the substance are associated with each other.

Referring to FIG. 6, the functions of non-invasive substance analysis apparatus 1 according to the present embodiment will be described by comparing Example 1 of the present embodiment with Comparative Examples 1-1 and 1-2.

In Example 1, substrate 11 is made of a material that does not allow excitation light 21 to pass therethrough (e.g., plastic or glass). In addition, in Example 1, a diameter of through hole 13 is 36 μm and a diameter of a light irradiation region 21b of excitation light 21 is 30 μm. Although Comparative Example 1-1 is similar to Example 1, through hole 13 is not formed in substrate 11. Although Comparative Example 1-2 is similar to Comparative Example 1-1, a transmittance of substrate 11 with respect to excitation light 21 is assumed to be 100% in Comparative Example 1-2. A normalized temperature variation in FIG. 6 is a temperature variation at each point of main surface 10a in each of Example 1, Comparative Example 1-1 and Comparative Example 1-2, which is normalized by a temperature variation at an edge of through hole 13 in main surface 10a in Example 1. The temperature variation at each point of main surface 10a is given by a difference between a temperature at each point of main surface 10a when sample 15 is not irradiated with excitation light 21 and a temperature at each point of main surface 10a when sample 15 is irradiated with excitation light 21.

In Example 1, through hole 13 is provided in sample support plate 10. Therefore, excitation light 21 reaches sample 15 at a stronger light intensity, without being absorbed by sample support plate 10. The absorption heat of sample 15 increases. In addition, a thermal conductivity of the air (0.024 W/(m•K)) in through hole 13 is lower than the thermal conductivity of substrate 11 (e.g., a thermal conductivity of plastic: equal to or more than about 0.1 W/(m•K) and about 0.3 W/(m•K), a thermal conductivity of glass: equal to or more than about 0.5 W/(m•K) and about 0.7 W/(m•K)). Therefore, the absorption heat of sample 15 becomes less likely to escape in a thickness direction (a direction in which main surface 10a and main surface 10b face each other) of sample support plate 10. The temperature variation of main surface 10a during analysis of sample 15 becomes larger. In Example 1, the substance in sample 15 or on the surface of sample 15 can be analyzed more accurately.

In contrast, in Comparative Example 1-1, substrate 11 is made of a material that does not allow excitation light 21 to pass therethrough. Therefore, excitation light 21 does not reach sample 15 and the absorption heat of sample 15 is not generated. The temperature variation of main surface 10a during analysis of sample 15 is zero. In Comparative Example 1-1, the substance in sample 15 or on the surface of sample 15 cannot be analyzed accurately.

In Comparative Example 1-2, the transmittance of substrate 11 with respect to excitation light 21 is assumed to be 100% and excitation light 21 reaches sample 15. Therefore, the temperature variation of main surface 10a during analysis of sample 15 is not zero. However, in Comparative Example 1-2, through hole 13 is not provided in substrate 11. Therefore, in Comparative Example 1-2, the absorption heat of sample 15 diffuses in the thickness direction (the direction in which main surface 10a and main surface 10b face each other) of sample support plate 10 more quickly than in Example 1. The temperature variation of main surface 10a in Comparative Example 1-2 is smaller than the temperature variation of main surface 10a in Example 1. In Comparative Example 1-2, the substance in sample 15 or on the surface of sample 15 cannot be analyzed accurately.

(Modification)

Sample support plate 10 (substrate 11) may be made of a material that is transparent to excitation light 21. The number of temperature sensors 25 and 26 may be three or more.

Temperature sensor 26 may be omitted and the number of temperature sensor 25 may be one. In this case, signal processing unit 37 is omitted. Substance analysis unit 38 receives the temperature variation signal of temperature sensor 25 from lock-in amplifier 34. Substance analysis unit 38 analyzes the substance in sample 15 or on the surface of sample 15 based on the temperature variation signal of temperature sensor 25. In step S3, the temperature variation signal of temperature sensor 25 is obtained, step S4 is omitted, and in step S5, the substance in sample 15 or on the surface of sample 15 is analyzed based on the temperature variation signal of temperature sensor 25.

Figure 7:
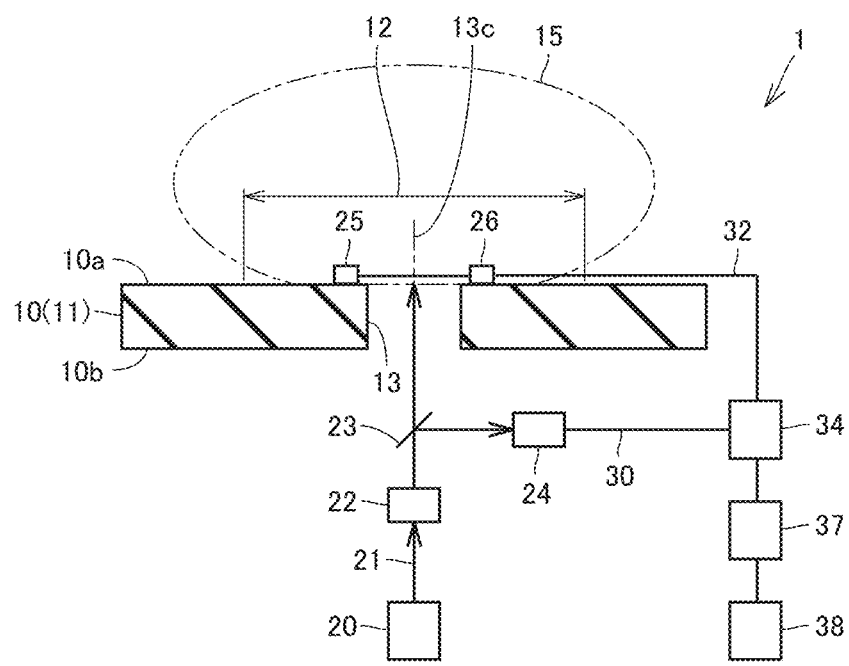
FIG. 7 is a schematic cross-sectional view of a non-invasive substance analysis apparatus according to a modification of the first embodiment.

As shown in FIG. 7, non-invasive substance analysis apparatus 1 may further include a beam splitter 23 and a photodetector 24. Excitation light 21 subjected to intensity modulation by optical chopper 22 enters beam splitter 23. Beam splitter 23 divides excitation light 21 into excitation light 21 traveling toward sample 15 and excitation light 21 traveling toward photodetector 24. Beam splitter 23 causes a part of excitation light 21 subjected to intensity modulation by optical chopper 22 to enter photodetector 24. Photodetector 24 detects the intensity of excitation light 21 subjected to intensity modulation. Photodetector 24 is, for example, a photodiode. Photodetector 24 is connected to lock-in amplifier 34 by electrical wire 30. Photodetector 24 outputs, to lock-in amplifier 34, the reference signal corresponding to the intensity of excitation light 21 subjected to intensity modulation.

According to the modification shown in FIG. 7, an influence of variations in intensity of excitation light 21 can be removed from the temperature variation signals of temperature sensors 25 and 26. Even when the intensity of excitation light 21 varies, the substance in sample 15 or on the surface of sample 15 can be analyzed more accurately.

The effects of non-invasive substance analysis apparatus 1 according to the present embodiment will be described.

Non-invasive substance analysis apparatus 1 according to the present embodiment includes: sample support plate 10; excitation light source 20; and at least one temperature sensor (e.g., temperature sensor 25, 26). Sample support plate 10 has a first main surface (main surface 10a) including sample placement region 12, and a second main surface (main surface 10b) opposite to the first main surface. Excitation light source 20 emits excitation light 21 toward sample 15 placed on sample placement region 12. The at least one temperature sensor is provided on the first main surface. Through hole 13 extending from sample placement region 12 to the second main surface is provided in sample support plate 10. Excitation light 21 is applied to sample 15 through through hole 13.

In non-invasive substance analysis apparatus 1, through hole 13 through which excitation light 21 passes is provided in sample support plate 10. Therefore, excitation light 21 reaches sample 15 at a stronger light intensity, without being absorbed by sample support plate 10. The absorption heat of sample 15 increases. In addition, the absorption heat of sample 15 becomes less likely to escape in the thickness direction (the direction in which the first main surface (main surface 10a) and the second main surface (main surface 10b) face each other) of sample support plate 10. The temperature signal output from the at least one temperature sensor (e.g., temperature sensor 25, 26) during irradiation of sample 15 with excitation light 21 increases. Therefore, the substance in sample 15 or on the surface of sample 15 can be analyzed more accurately.

In non-invasive substance analysis apparatus 1, a material that is opaque to excitation light 21 can be used as sample support plate 10 (substrate 11). A wide range of choice of the material of sample support plate 10 (substrate 11) is offered. By using a material (e.g., plastic or glass) that is opaque to excitation light 21 but has a low thermal conductivity as the material of sample support plate 10 (substrate 11), the temperature signal output from the at least one temperature sensor (e.g., temperature sensor 25, 26) during irradiation of sample 15 with excitation light 21 increases. Therefore, the substance in sample 15 or on the surface of sample 15 can be analyzed more accurately.

In non-invasive substance analysis apparatus 1 according to the present embodiment, the at least one temperature sensor (e.g., temperature sensor 25, 26) is provided in sample placement region 12 and comes into contact with sample 15.

Therefore, the absorption heat of sample 15 is efficiently conducted to the at least one temperature sensor (e.g., temperature sensor 25, 26). The temperature signal output from the at least one temperature sensor during irradiation of sample 15 with excitation light 21 increases. The substance in sample 15 or on the surface of sample 15 can be analyzed more accurately.

Non-invasive substance analysis apparatus 1 according to the present embodiment further includes substance analysis unit 38. Substance analysis unit 38 analyzes the substance in sample 15 or on the surface of sample 15 based on the temperature variation signal of the at least one temperature sensor (e.g., temperature sensor 25, 26). The temperature variation signal of the at least one temperature sensor corresponds to a temperature variation of sample 15 measured by the at least one temperature sensor during analysis of sample 15.

Noise included in the temperature signal output from the at least one temperature sensor (e.g., temperature sensor 25, 26) is removed from the temperature variation signal. The substance in sample 15 or on the surface of sample 15 can be analyzed more accurately.

Non-invasive substance analysis apparatus 1 according to the present embodiment further includes signal processing unit 37 and substance analysis unit 38. The at least one temperature sensor includes a plurality of temperature sensors 25 and 26. Signal processing unit 37 outputs an average of a plurality of temperature variation signals. Each of the plurality of temperature variation signals corresponds to a temperature variation of sample 15 measured by a corresponding one of the plurality of temperature sensors 25 and 26 during analysis of sample 15. Substance analysis unit 38 analyzes the substance in sample 15 or on the surface of sample 15 based on the average of the plurality of temperature variation signals.

Noise included in the temperature signals output from temperature sensors 25 and 26 is removed from the temperature variation signals. In addition, the average of the plurality of temperature variation signals reduces variations among the plurality of temperature variation signals. Therefore, the substance in sample 15 or on the surface of sample 15 can be analyzed more accurately.

In non-invasive substance analysis apparatus 1 according to the present embodiment, the at least one temperature sensor (e.g., temperature sensor 25, 26) includes temperature sensor main body 27. Temperature sensor main body 27 is a thermocouple, a thermopile, a thermistor, or a diode.

Therefore, the probe light source that emits the probe light to measure the absorption heat of sample 15 and the optical position sensor that detects deflection of the probe light become unnecessary. Non-invasive substance analysis apparatus 1 can be reduced in size.

The at least one temperature sensor (e.g., temperature sensor 25, 26) further includes protective film 28 that covers temperature sensor main body 27.

Protective film 28 prevents sample 15 from coming into contact with temperature sensor main body 27. Therefore, the lifetime of temperature sensor main body 27 is lengthened.

Second Embodiment

Figure 8:
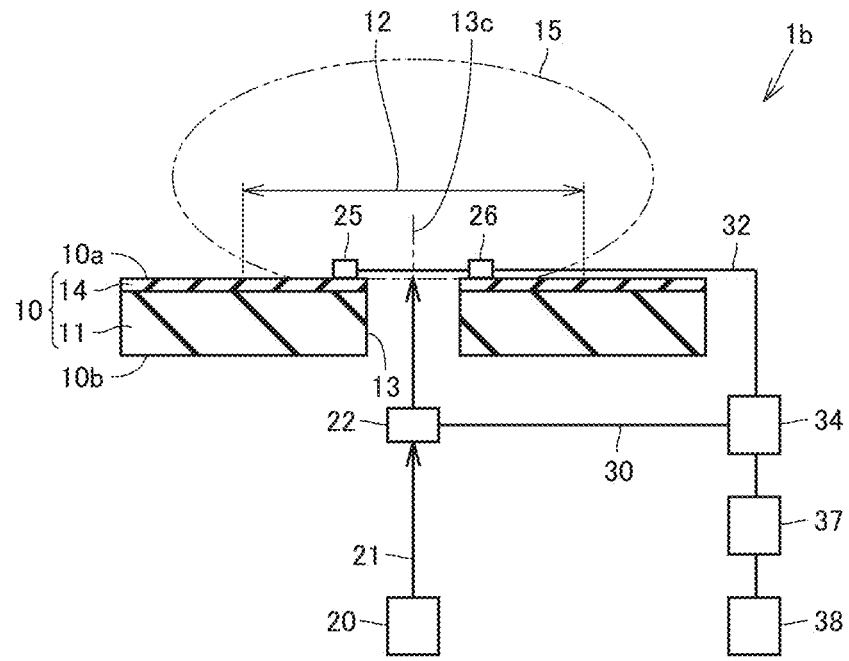
FIG. 8 is a schematic cross-sectional view of a non-invasive substance analysis apparatus according to a second embodiment.

A non-invasive substance analysis apparatus 1b according to a second embodiment will be described with reference to FIG. 8. Although non-invasive substance analysis apparatus 1b according to the present embodiment is configured similarly to non-invasive substance analysis apparatus 1 according to the first embodiment, non-invasive substance analysis apparatus 1b according to the present embodiment is different from non-invasive substance analysis apparatus 1 according to the first embodiment mainly in the following points.

In non-invasive substance analysis apparatus 1b, sample support plate 10 includes a low-thermal-conductivity film 14, in addition to substrate 11.

Substrate 11 according to the present embodiment has a thermal conductivity higher than that of substrate 11 according to the first embodiment. In the present embodiment, the thermal conductivity of substrate 11 may be higher than that of sample 15. In the present embodiment, substrate 11 is made of, for example, a semiconductor substrate such as silicon (thermal conductivity: about 160 W/(m•K)). Since substrate 11 is made of a semiconductor material, through hole 13 having a small size (e.g., a diameter of several tens of micrometers) can be easily formed using a semiconductor micromachining process.

Low-thermal-conductivity film 14 is provided on substrate 11. Low-thermal-conductivity film 14 has a thermal conductivity lower than that of substrate 11. The thermal conductivity of low-thermal-conductivity film 14 is, for example, equal to or less than 20% of the thermal conductivity of substrate 11. The thermal conductivity of low-thermal-conductivity film 14 may be equal to or less than 10% of the thermal conductivity of substrate 11, may be equal to or less than 5% of the thermal conductivity of substrate 11, may be equal to or less than 2% of the thermal conductivity of substrate 11, or may be equal to or less than 1% of the thermal conductivity of substrate 11. Low-thermal-conductivity film 14 is made of, for example, silicon dioxide (thermal conductivity: 1.4 W/(m•K)).

Main surface 10a is formed by low-thermal-conductivity film 14. A part of main surface 10a may be formed by low-thermal-conductivity film 14. Sample placement region 12 is formed by low-thermal-conductivity film 14. Each of temperature sensors 25 and 26 is provided on low-thermal-conductivity film 14. Through hole 13 is provided in both of substrate 11 and low-thermal-conductivity film 14.

Figure 9:
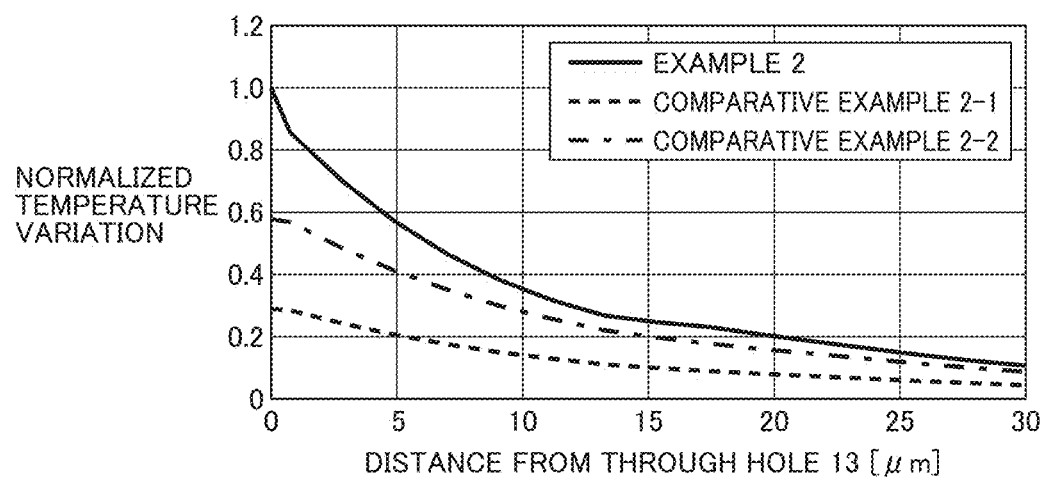
FIG. 9 is a diagram showing simulation results of normalized temperature variations in Example 2 and Comparative Examples 2-1 and 2-2.

Referring to FIG. 9, the functions of non-invasive substance analysis apparatus 1b according to the present embodiment will be described by comparing Example 2 of the present embodiment with Comparative Examples 2-1 and 2-2.

In Example 2, substrate 11 is made of silicon and low-thermal-conductivity film 14 is made of silicon dioxide. In addition, in Example 2, a diameter of through hole 13 is 36 μm and a diameter of light irradiation region 21b of excitation light 21 is 30 μm. Although Comparative Example 2-1 is similar to Example 2, through hole 13 is not formed in substrate 11. Although Comparative Example 2-2 is similar to Comparative Example 2-1, a transmittance of substrate 11 with respect to excitation light 21 is assumed to be 100% in Comparative Example 2-2. A normalized temperature variation in FIG. 9 is a temperature variation at each point of main surface 10a in each of Example 2, Comparative Example 2-1 and Comparative Example 2-2, which is normalized by a temperature variation at an edge of through hole 13 in main surface 10a in Example 2. The temperature variation at each point of main surface 10a is given by a difference between a temperature at each point of main surface 10a when sample 15 is not irradiated with excitation light 21 and a temperature at each point of main surface 10a when sample 15 is irradiated with excitation light 21.

In Example 2, through hole 13 is provided in sample support plate 10. Therefore, excitation light 21 reaches sample 15 at a stronger light intensity, without being absorbed by sample support plate 10. The absorption heat of sample 15 increases. In addition, the thermal conductivity of the air (0.024 W/(m•K)) in through hole 13 is lower than the thermal conductivity of substrate 11 (e.g., thermal conductivity of silicon: about 160 W/(m•K)). Therefore, the absorption heat of sample 15 becomes less likely to escape in the thickness direction (the direction in which main surface 10a and main surface 10b face each other) of sample support plate 10. The temperature variation of main surface 10a during analysis of sample 15 becomes larger. In Example 2, the substance in sample 15 or on the surface of sample 15 can be analyzed more accurately.

In contrast, in Comparative Example 2-1, although through hole 13 is not provided in sample support plate 10, substrate 11 is made of silicon and allows excitation light 21 to pass therethrough. Therefore, excitation light 21 reaches sample 15 and the temperature variation of main surface 10a is not zero. However, in Comparative Example 2-1, a part of excitation light 21 is reflected at main surface 10b or absorbed by substrate 11. Therefore, the intensity of excitation light 21 reaching sample 15 in Comparative Example 2-1 is lower than the intensity of excitation light 21 reaching sample 15 in Example 2. Furthermore, in Comparative Example 2-1, the absorption heat of sample 15 diffuses in the thickness direction (the direction in which main surface 10a and main surface 10b face each other) of sample support plate 10 more quickly than in Example 2. As a result, the temperature variation of main surface 10a in Comparative Example 2-1 is smaller than the temperature variation of main surface 10a in Example 2. In Comparative Example 2-1, the substance in sample 15 or on the surface of sample 15 cannot be analyzed accurately.

In Comparative Example 2-2, through hole 13 is not provided in substrate 11. Therefore, in Comparative Example 2-2, the absorption heat of sample 15 diffuses in the thickness direction (the direction in which main surface 10a and main surface 10b face each other) of sample support plate 10 more quickly than in Example 2. The temperature variation of main surface 10a in Comparative Example 2-2 is smaller than the temperature variation of main surface 10a in Example 2. In Comparative Example 2-2, the substance in sample 15 or on the surface of sample 15 cannot be analyzed accurately.

Non-invasive substance analysis apparatus 1b according to the present embodiment further provides the following effects, in addition to the effects of non-invasive substance analysis apparatus 1 according to the first embodiment.

In non-invasive substance analysis apparatus 1b according to the present embodiment, sample support plate 10 includes substrate 11 and low-thermal-conductivity film 14. Low-thermal-conductivity film 14 is provided on substrate 11 and has a thermal conductivity lower than that of substrate 11. At least a part of the first main surface (main surface 10a) is formed by low-thermal-conductivity film 14. The at least one temperature sensor (e.g., temperature sensor 25, 26) is provided on low-thermal-conductivity film 14.

Low-thermal-conductivity film 14 makes it less likely that the absorption heat of sample 15 escapes in the thickness direction (the direction in which main surface 10a and main surface 10b face each other) of sample support plate 10. The temperature signal output from the at least one temperature sensor (e.g., temperature sensor 25, 26) during irradiation of sample 15 with excitation light 21 increases. Therefore, the substance in sample 15 or on the surface of sample 15 can be analyzed more accurately.

Third Embodiment

Figure 10:
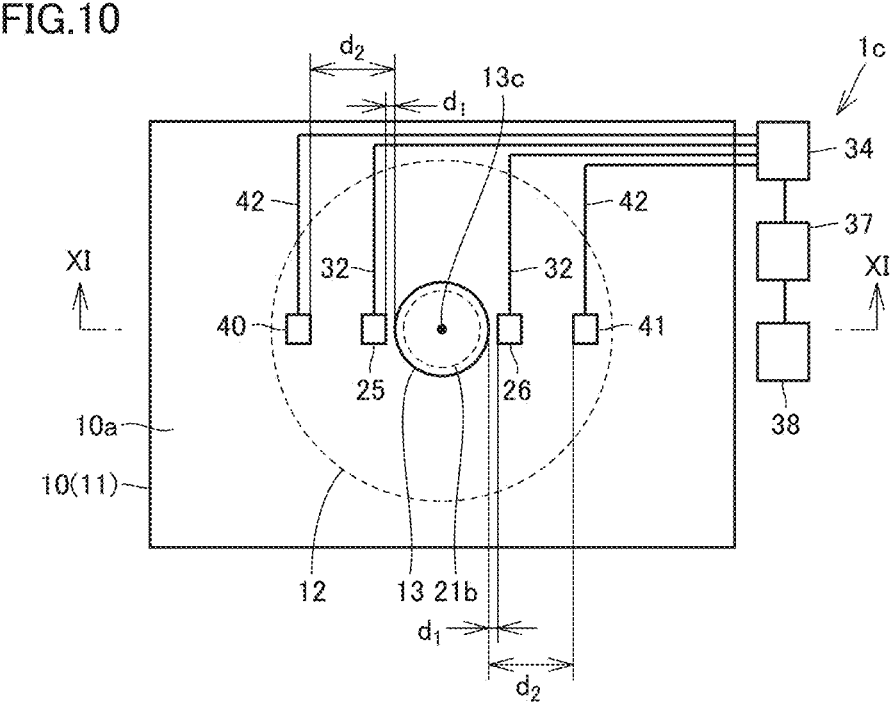
FIG. 10 is a schematic plan view of a non-invasive substance analysis apparatus according to a third embodiment.
Figure 11:
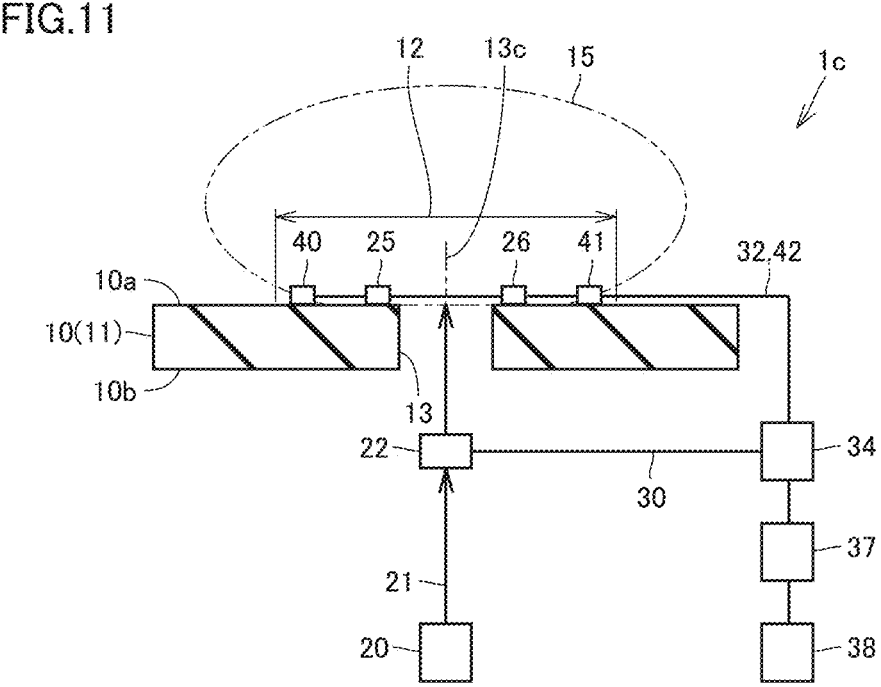
FIG. 11 is a schematic cross-sectional view of the non-invasive substance analysis apparatus according to the third embodiment taken along a cross-sectional line XI-XI shown in FIG. 10.

A non-invasive substance analysis apparatus 1c according to a third embodiment will be described with reference to FIGS. 10 and 11. Although non-invasive substance analysis apparatus 1c according to the present embodiment is configured similarly to non-invasive substance analysis apparatus 1 according to the first embodiment, non-invasive substance analysis apparatus 1c according to the present embodiment is different from non-invasive substance analysis apparatus 1 according to the first embodiment mainly in the following points.

Non-invasive substance analysis apparatus 1c further includes reference temperature sensors 40 and 41. Reference temperature sensors 40 and 41 are configured similarly to temperature sensors 25 and 26. Specifically, each of reference temperature sensors 40 and 41 includes temperature sensor main body 27 (see FIG. 3). Each of reference temperature sensors 40 and 41 may further include protective film 28 (see FIG. 3) that covers temperature sensor main body 27.

Each of reference temperature sensors 40 and 41 is provided on main surface 10a. Each of reference temperature sensors 40 and 41 is provided in sample placement region 12 and comes into contact with sample 15. Each of reference temperature sensors 40 and 41 outputs a reference temperature signal corresponding to the temperature of sample 15 to lock-in amplifier 34 by an electrical wire 42. Specifically, reference temperature sensor 40 outputs a reference temperature signal corresponding to a temperature of a portion of sample 15 with which reference temperature sensor 40 is in contact. Reference temperature sensor 41 outputs a reference temperature signal corresponding to a temperature of a portion of sample 15 with which reference temperature sensor 41 is in contact.

When sample 15 is a living body, thermal variations of sample 15 (such as, for example, variations in body temperature of the living body) or movement of sample 15 (such as, for example, contraction or relaxation of a muscle included in sample 15 or variations in position of sample 15) may occur during analysis of the substance in sample 15 or on the surface of sample 15. Each of reference temperature sensors 40 and 41 detects temperature variations caused by the thermal variations or movement of sample 15, without being affected by the absorption heat of sample 15. Therefore, a distance $d_2$ between each of reference temperature sensors 40 and 41 and through hole 13 is longer than a distance $d_1$ between each of temperature sensors 25 and 26 and through hole 13 in a plan view of main surface 10a. Distance $d_2$ is, for example, ten times or more as long as distance $d_1$. Distance $d_2$ may be twenty times or more as long as distance $d_1$. In one example, distance $d_1$ is 5 μm and distance $d_2$ is 200 μm.

Reference temperature sensors 40 and 41 are disposed to be rotationally symmetrical with respect to central axis 13c of through hole 13 in a plan view of main surface 10a. Therefore, each of reference temperature sensors 40 and 41 can more accurately detect the temperature variations caused by the thermal variations or movement of sample 15.

Reference temperature sensor 40 is disposed in the same direction as temperature sensor 25 with respect to central axis 13c of through hole 13 in a plan view of main surface 10a. Therefore, variations in reference temperature signal of reference temperature sensor 40 caused by the thermal variations or movement of sample 15 during analysis of sample 15 are similar to the variations in temperature signal of temperature sensor 25 caused by the thermal variations or movement of sample 15 during analysis of sample 15. Reference temperature sensor 40 can more accurately detect the variations in temperature signal of temperature sensor 25 caused by the thermal variations or movement of sample 15 during analysis of sample 15, without being affected by the absorption heat of sample 15.

Reference temperature sensor 41 is disposed in the same direction as temperature sensor 26 with respect to central axis 13c of through hole 13 in a plan view~ 24~ of main surface 10a. Therefore, variations in temperature signal of reference temperature sensor 41 caused by the thermal variations or movement of sample 15 during analysis of sample 15 are similar to the variations in temperature signal of temperature sensor 26 caused by the thermal variations or movement of sample 15 during analysis of sample 15. Reference temperature sensor 41 can more accurately detect the variations in temperature signal of temperature sensor 26 caused by the thermal variations or movement of sample 15 during analysis of sample 15, without being affected by the absorption heat of sample 15.

Similarly to the first embodiment, lock-in amplifier 34 outputs the temperature variation signal of temperature sensor 25 and the temperature variation signal of temperature sensor 26 to signal processing unit 37. The temperature variation signal of temperature sensor 25 and the temperature variation signal of temperature sensor 26 are affected by the variations in temperature signals caused by the thermal variations or movement of sample 15 during analysis of sample 15, in addition to the absorption heat of sample 15. In order to accurately analyze the substance in sample 15 or on the surface of sample 15, it is necessary to remove the influence of the variations in temperature signals caused by the thermal variations or movement of sample 15 during analysis of sample 15 from the temperature variation signal of temperature sensor 25 and the temperature variation signal of temperature sensor 26.

Thus, signal processing unit 37 receives the reference temperature signal of reference temperature sensor 40 and the reference temperature signal of reference temperature sensor 41. Signal processing unit 37 calculates a variation of the reference temperature signal of reference temperature sensor 40 during analysis of sample 15 as a reference temperature variation signal of reference temperature sensor 40. Signal processing unit 37 calculates a variation of the reference temperature signal of reference temperature sensor 41 during analysis of sample 15 as a reference temperature variation signal of reference temperature sensor 41.

Signal processing unit 37 calculates a difference between the temperature variation signal of temperature sensor 25 and the reference temperature variation signal of reference temperature sensor 40 as a calibrated temperature variation signal of temperature sensor 25. The calibrated temperature variation signal of temperature sensor 25 is a temperature variation signal of temperature sensor 25 due to the absorption heat of sample 15, from which the influence of the variations in temperature signal caused by the thermal variations or movement of sample 15 during analysis of sample 15 has been removed. Similarly, signal processing unit 37 calculates a difference between the temperature variation signal of temperature sensor 26 and the reference temperature variation signal of reference temperature sensor 41 as a calibrated temperature variation signal of temperature sensor 26. The calibrated temperature variation signal of temperature sensor 26 is a temperature variation signal of temperature sensor 26 due to the absorption heat of sample 15, from which the influence of the variations in temperature signal caused by the thermal variations or movement of sample 15 during analysis of sample 15 has been removed.

Signal processing unit 37 calculates an average of the calibrated temperature variation signal of temperature sensor 25 and the calibrated temperature variation signal of temperature sensor 26 as an average calibrated temperature variation signal. Substance analysis unit 38 analyzes the substance in sample 15 or on the surface of sample 15 based on the average calibrated temperature variation signal.

(Modification)

Temperature sensor 26 may be omitted and the number of temperature sensor 25 may be one. In this case, signal processing unit 37 outputs the calibrated temperature variation signal of temperature sensor 25 to substance analysis unit 38. Substance analysis unit 38 analyzes the substance in sample 15 or on the surface of sample 15 based on the calibrated temperature variation signal of temperature sensor 25.

Non-invasive substance analysis apparatus 1c according to the present embodiment further provides the following effects, in addition to the effects of non-invasive substance analysis apparatus 1 according to the first embodiment. Non-invasive substance analysis apparatus 1c according to the present embodiment further includes reference temperature sensor 40, 41 provided on the first main surface (main surface 10a). Reference temperature sensor 40, 41 is provided in sample placement region 12 and comes into contact with sample 15. In a plan view of the first main surface, a second distance (distance $d_2$) between each of reference temperature sensors 40 and 41 and through hole 13 is ten times or more as long as a first distance (distance $d_1$) between each of temperature sensors 25 and 26 and through hole 13.

Each of reference temperature sensors 40 and 41 detects the temperature variations during analysis of sample 15, without being affected by the absorption heat of sample 15. Therefore, each of reference temperature sensors 40 and 41 can more accurately detect the temperature variations caused by the absorption heat of sample 15, without being affected by the variations in temperature signal caused by the thermal variations or movement of sample 15 during analysis of sample 15. The substance in sample 15 or on the surface of sample 15 can be analyzed more accurately.

In non-invasive substance analysis apparatus 1c according to the present embodiment, signal processing unit 37 calculates the calibrated temperature variation signal of the at least one temperature sensor by calibrating the temperature variation signal of the at least one temperature sensor (e.g., temperature sensor 25, 26) with the reference temperature variation signal of reference temperature sensor 40, 41. Substance analysis unit 38 analyzes the substance in sample 15 or on the surface of sample 15 based on the calibrated temperature variation signal of the at least one temperature sensor.

By calibrating the temperature variation signal of the at least one temperature sensor (e.g., temperature sensor 25, 26) with the reference temperature variation signal of each of reference temperature sensors 40 and 41, the temperature variations caused by the absorption heat of sample 15 can be detected more accurately, without being affected by the variations in temperature signal caused by the thermal variations or movement of sample 15 during analysis of sample 15. Therefore, the substance in sample 15 or on the surface of sample 15 can be analyzed more accurately.

Fourth Embodiment

Figure 12:
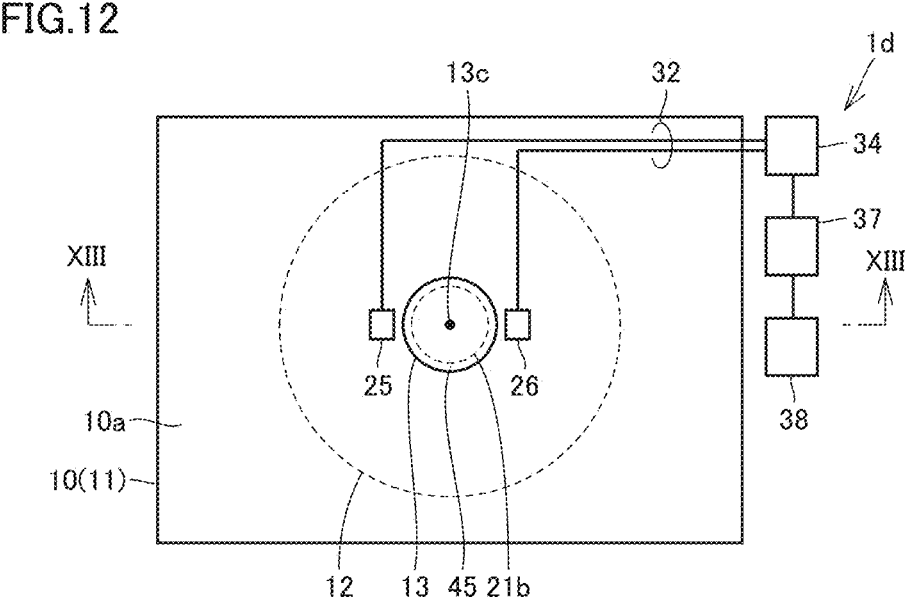
FIG. 12 is a schematic plan view of a non-invasive substance analysis apparatus according to a fourth embodiment.
Figure 13:
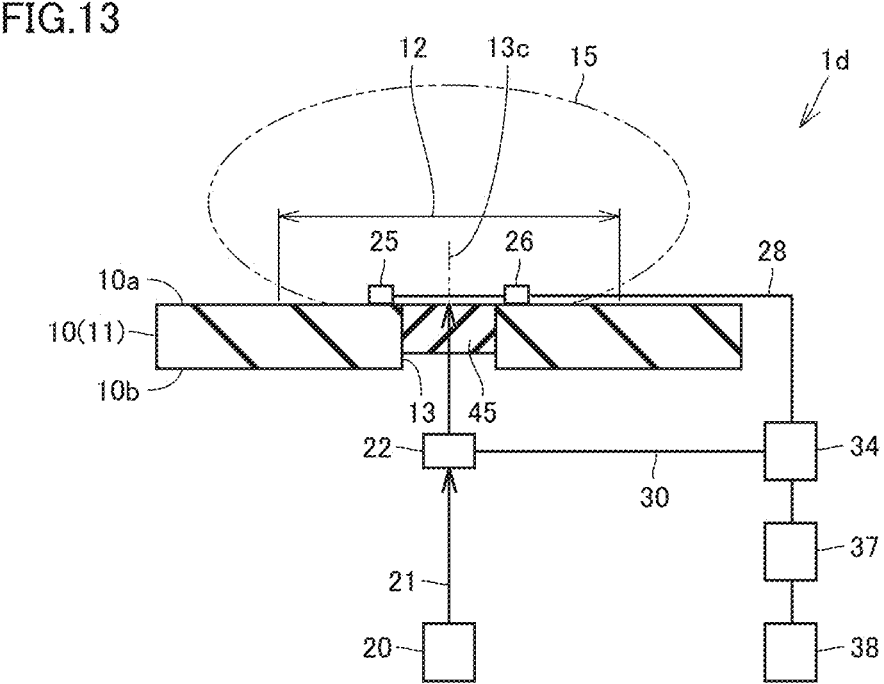
FIG. 13 is a schematic cross-sectional view of the non-invasive substance analysis apparatus according to the fourth embodiment taken along a cross-sectional line XIII-XIII shown in FIG. 12.

A non-invasive substance analysis apparatus 1d according to a fourth embodiment will be described with reference to FIGS. 12 and 13. Although non-invasive substance analysis apparatus 1d according to the present embodiment is configured similarly to non-invasive substance analysis apparatus 1 according to the first embodiment, non-invasive substance analysis apparatus 1d according to the present embodiment is different from non-invasive substance analysis apparatus 1 according to the first embodiment mainly in the following points.

Non-invasive substance analysis apparatus 1d further includes an optical medium 45. Optical medium 45 allows excitation light 21 to pass therethrough. A transmittance of optical medium 45 with respect to excitation light 21 is higher than the transmittance of sample support plate 10 (substrate 11) with respect to excitation light 21. When excitation light 21 is mid-infrared light, optical medium 45 is made of, for example, chalcogenide glass (SSbSnGe).

Optical medium 45 closes through hole 13. A part of sample placement region 12 is formed by optical medium 45. The whole of sample placement region 12 may be formed by optical medium 45. Sample 15 can be placed on optical medium 45. A part of through hole 13 is filled with optical medium 45. A portion of through hole 13 that is more proximal to main surface 10b than optical medium 45 is a cavity that is not filled with optical medium 45. Excitation light 21 is applied to sample 15 through optical medium 45 and the cavity. The whole of through hole 13 may be filled with optical medium 45.

A thermal conductivity of optical medium 45 is lower than the thermal conductivity of substrate 11. The thermal conductivity of optical medium 45 may be equal to or less than 10% of the thermal conductivity of substrate 11, may be equal to or less than 5% of the thermal conductivity of substrate 11, or may be equal to or less than 2% of the thermal conductivity of substrate 11. For example, substrate 11 is made of silicon (thermal conductivity: about 160 W/(m•K)) and optical medium 45 is made of chalcogenide glass (thermal conductivity: 0.36 W/(m•K)). The thermal conductivity of the air (0.024 W/(m•K)) in the cavity is lower than the thermal conductivity of substrate 11.

Non-invasive substance analysis apparatus 1d according to the present embodiment provides the following effects similar to the effects of non-invasive substance analysis apparatus 1 according to the first embodiment.

Non-invasive substance analysis apparatus 1d according to the present embodiment further includes optical medium 45 that allows excitation light 21 to pass therethrough. Optical medium 45 closes through hole 13. At least a part of sample placement region 12 is formed by optical medium 45. Excitation light 21 is applied to sample 15 through optical medium 45.

Therefore, excitation light 21 reaches sample 15 at a stronger light intensity, without being absorbed by sample support plate 10. The absorption heat of sample 15 increases. In addition, the absorption heat of sample 15 becomes less likely to escape in the thickness direction (the direction in which the first main surface (main surface 10a) and the second main surface (main surface 10b) face each other) of sample support plate 10. The temperature signal output from each of temperature sensors 25 and 26 during irradiation of sample 15 with excitation light 21 increases. The substance in sample 15 or on the surface of sample 15 can be analyzed more accurately.

Sample 15 can be placed on optical medium 45. Therefore, even when the size of sample 15 is smaller than the size of through hole 13, or even when sample 15 is a liquid, the substance in sample 15 or on the surface of sample 15 can be analyzed.

Optical medium 45 that is transparent to excitation light 21 such as mid-infrared light is more expensive and lower in mechanical strength than sample support plate 10 (substrate 11). Since optical medium 45 is provided in through hole 13 of sample support plate 10 (substrate 11), an amount of used optical medium 45 is reduced, as compared with when the whole of sample support plate 10 (substrate 11) is formed by optical medium 45. Therefore, the mechanical strength of non-invasive substance analysis apparatus 1d can be increased and the cost of non-invasive substance analysis apparatus 1d can be reduced.

In non-invasive substance analysis apparatus 1d according to the present embodiment, sample support plate 10 includes substrate 11. Optical medium 45 has a thermal conductivity lower than that of substrate 11.

Therefore, the absorption heat of sample 15 becomes less likely to escape in the thickness direction (the direction in which the first main surface (main surface 10a) and the second main surface (main surface 10b) face each other) of sample support plate 10. The temperature signal output from each of temperature sensors 25 and 26 during irradiation of sample 15 with excitation light 21 increases. Therefore, the substance in sample 15 or on the surface of sample 15 can be analyzed more accurately.

Fifth Embodiment

Figure 14:
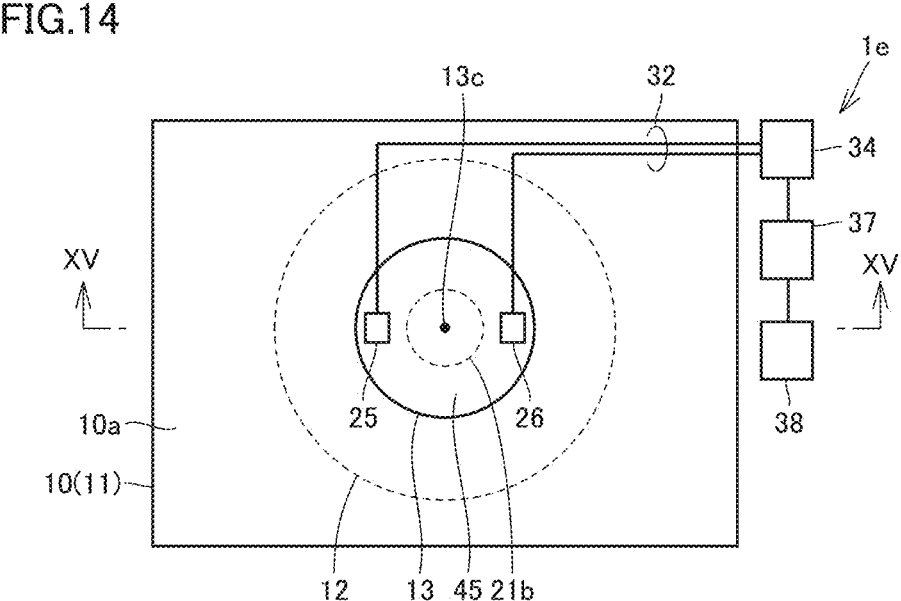
FIG. 14 is a schematic plan view of a non-invasive substance analysis apparatus according to a fifth embodiment.
Figure 15:
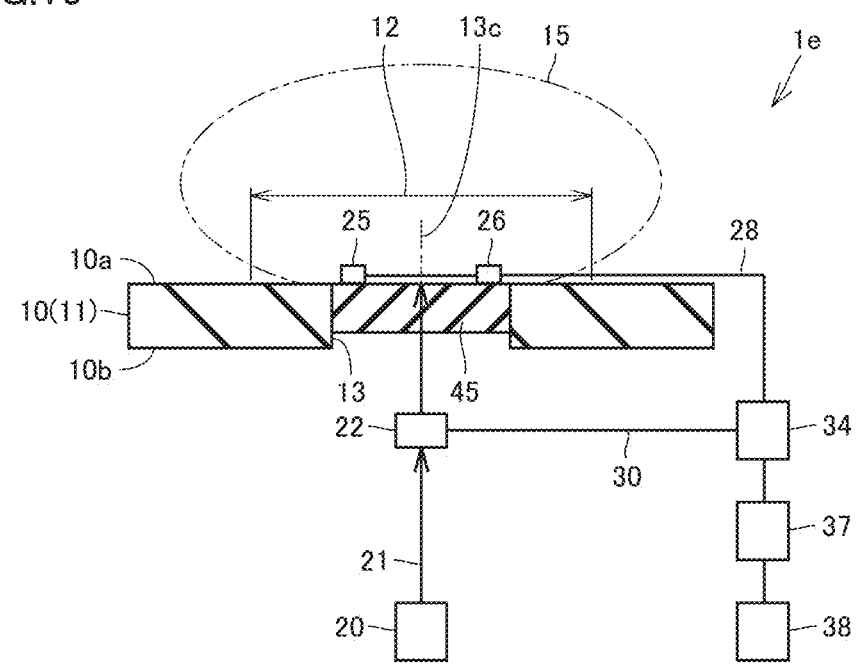
FIG. 15 is a schematic cross-sectional view of the non-invasive substance analysis apparatus according to the fifth embodiment taken along a cross-sectional line XV-XV shown in FIG. 14.

A non-invasive substance analysis apparatus 1e according to a fifth embodiment will be described with reference to FIGS. 14 and 15. Although non-invasive substance analysis apparatus 1e according to the present embodiment is configured similarly to non-invasive substance analysis apparatus 1d according to the fourth embodiment, non-invasive substance analysis apparatus 1e according to the present embodiment is different from non-invasive substance analysis apparatus 1d according to the fourth embodiment mainly in the following points.

In a plan view of main surface 10a, the size of through hole 13 according to the present embodiment is larger than the size of through hole 13 according to the fourth embodiment and the size of optical medium 45 according to the present embodiment is larger than the size of optical medium 45 according to the fourth embodiment. For example, each of the diameter of through hole 13 and the diameter of optical medium 45 according to the present embodiment is 200 μm in a plan view of main surface 10a. In the present embodiment, each of temperature sensors 25 and 26 is disposed on optical medium 45. Similarly to the fourth embodiment, in the present embodiment as well, the thermal conductivity of optical medium 45 is lower than the thermal conductivity of substrate 11. Each of temperature sensors 25 and 26 is disposed outside light irradiation region 21b of excitation light 21 in a plan view of main surface 10a.

Non-invasive substance analysis apparatus 1e according to the present embodiment further provides the following effects, in addition to the effects of non-invasive substance analysis apparatus 1d according to the fourth embodiment.

In non-invasive substance analysis apparatus 1e according to the present embodiment, the at least one temperature sensor (e.g., temperature sensor 25, 26) is disposed on optical medium 45 having a thermal conductivity lower than that of substrate 11.

Therefore, the absorption heat of sample 15 also becomes less likely to escape in a direction in which the first main surface extends, in addition to the thickness direction (the direction in which the first main surface (main surface 10a) and the second main surface (main surface 10b) face each other) of sample support plate 10. The temperature signal output from the at least one temperature sensor (e.g., temperature sensor 25, 26) during irradiation of sample 15 with excitation light 21 increases. Therefore, the substance in sample 15 or on the surface of sample 15 can be analyzed more accurately.

Sixth Embodiment

Figure 16:
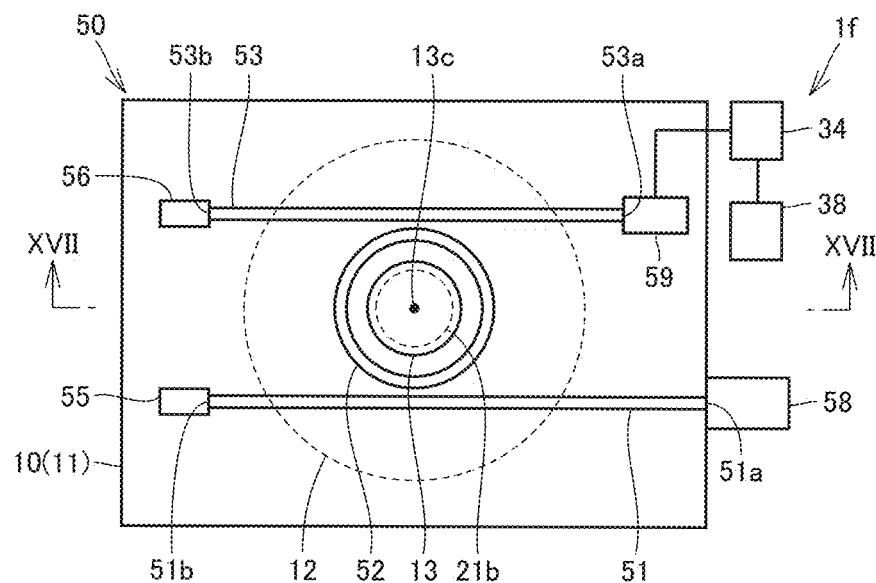
FIG. 16 is a schematic plan view of a non-invasive substance analysis apparatus according to a sixth embodiment.
Figure 17:
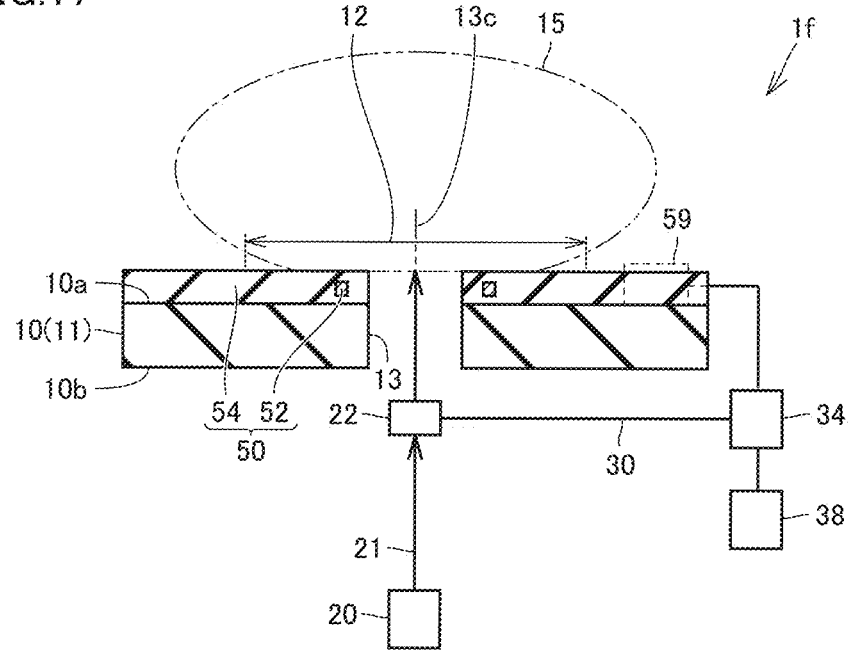
FIG. 17 is a schematic cross-sectional view of the non-invasive substance analysis apparatus according to the sixth embodiment taken along a cross-sectional line XVII-XVII shown in FIG. 16.

A non-invasive substance analysis apparatus 1f according to a sixth embodiment will be described with reference to FIGS. 16 and 17. Although non-invasive substance analysis apparatus 1f according to the present embodiment is configured similarly to non-invasive substance analysis apparatus 1 according to the first embodiment, non-invasive substance analysis apparatus 1f according to the present embodiment is different from non-invasive substance analysis apparatus 1 according to the first embodiment mainly in the following points.

Non-invasive substance analysis apparatus 1f includes a temperature sensor 50, instead of temperature sensors 25 and 26 (see FIGS. 1 and 2). Temperature sensor 50 includes a first optical waveguide 51, a waveguide-type ring resonator 52, a second optical waveguide 53, and a clad layer 54. Temperature sensor 50 may further include terminal portions 55 and 56.

Substrate 11 supports first optical waveguide 51, waveguide-type ring resonator 52, second optical waveguide 53, and clad layer 54. Substrate 11 has main surface 10b. Substrate 11 is, for example, a silicon substrate.

Probe light emitted from a probe light source 58 enters first optical waveguide 51. A wavelength of the probe light may be shorter than the wavelength of excitation light 21. For example, probe light source 58 is a laser diode for optical communication and the wavelength of the probe light is equal to or more than 1100 nm and equal to or less than 1700 nm.

First optical waveguide 51 includes an end 51a on which the probe light is incident, and an end 51b opposite to end 51a. First optical waveguide 51 has a refractive index higher than that of clad layer 54. The probe light propagates through first optical waveguide 51. First optical waveguide 51 is, for example, a silicon waveguide.

Waveguide-type ring resonator 52 is optically coupled to first optical waveguide 51. Waveguide-type ring resonator 52 has a refractive index higher than that of clad layer 54. The probe light propagates through waveguide-type ring resonator 52. Waveguide-type ring resonator 52 has the thermo-optical effect. Waveguide-type ring resonator 52 is, for example, a silicon waveguide. A thermo-optical coefficient of silicon is $2.3 \times 10^{-4}$ ($K^{-1}$). Silicon has a relatively large thermo-optical coefficient among optical materials for optical waveguides. Through hole 13 is formed inside waveguide-type ring resonator 52.

Second optical waveguide 53 is optically coupled to waveguide-type ring resonator 52. Second optical waveguide 53 has a refractive index higher than that of clad layer 54. The probe light propagates through second optical waveguide 53. Second optical waveguide 53 is disposed symmetrically to first optical waveguide 51 with respect to waveguide-type ring resonator 52 in a plan view of main surface 10a. Second optical waveguide 53 includes an end 53a optically coupled to a light intensity detector 59, and an end 53b opposite to end 53a. Ends 51a and 53a are located on the same side with respect to waveguide-type ring resonator 52. Ends 51b and 53b are located on the same side with respect to waveguide-type ring resonator 52.

Clad layer 54 separates first optical waveguide 51, waveguide-type ring resonator 52 and second optical waveguide 53 from substrate 11. Clad layer 54 covers first optical waveguide 51, waveguide-type ring resonator 52 and second optical waveguide 53. Clad layer 54 has main surface 10a. A thermal conductivity of clad layer 54 is smaller than the thermal conductivity of substrate 11. Clad layer 54 is made of, for example, silica-based glass.

Terminal portion 55 is provided at end 51b of first optical waveguide 51. Terminal portion 56 is provided at end 53b of second optical waveguide 53. Each of terminal portions 55 and 56 scatters or absorbs the probe light and reduces the return light of the probe light traveling to waveguide-type ring resonator 52, probe light source 58 and light intensity detector 59. Each of terminal portions 55 and 56 includes, for example, a tapered waveguide that easily scatters the light outside the waveguide, and an electrode (e.g., a metal electrode) that absorbs the scattered light.

The absorption of excitation light 21 by the substance in sample 15 or on the surface of sample 15 causes sample 15 to generate absorption heat. The absorption heat of sample 15 is conducted to waveguide-type ring resonator 52, which causes a change in temperature of waveguide-type ring resonator 52. Waveguide-type ring resonator 52 has the thermo-optical effect. Therefore, when the temperature of waveguide-type ring resonator 52 changes, the refractive index of waveguide-type ring resonator 52 changes, which causes a change in coupling rate of the probe light from first optical waveguide 51 to second optical waveguide 53 through waveguide-type ring resonator 52.

Light intensity detector 59 is, for example, a photodiode. Light intensity detector 59 detects a light intensity of the probe light from first optical waveguide 51 to second optical waveguide 53 through waveguide-type ring resonator 52. Light intensity detector 59 is connected to lock-in amplifier 34. Light intensity detector 59 outputs a light intensity signal of the probe light to lock-in amplifier 34.

Lock-in amplifier 34 performs synchronous detection of the light intensity signal of the probe light received from light intensity detector 59 with the excitation light intensity signal received from photodetector 24. Lock-in amplifier 34 outputs a DC component proportional to an amplitude of the light intensity signal of light intensity detector 59. The DC component corresponds to a temperature variation of sample 15 during analysis of sample 15, and is a temperature variation signal of temperature sensor 50. Lock-in amplifier 34 outputs the temperature variation signal of temperature sensor 50 to substance analysis unit 38.

Substance analysis unit 38 receives the temperature variation signal of temperature sensor 50 from lock-in amplifier 34. Substance analysis unit 38 analyzes the substance in sample 15 or on the surface of sample 15 based on the temperature variation signal of temperature sensor 50.

Non-invasive substance analysis apparatus 1f according to the present embodiment provides the following effects similar to the effects of non-invasive substance analysis apparatus 1 according to the first embodiment.

In non-invasive substance analysis apparatus 1f according to the present embodiment, temperature sensor 50 includes first optical waveguide 51 on which the probe light is incident, waveguide-type ring resonator 52 optically coupled to first optical waveguide 51, and second optical waveguide 53 optically coupled to waveguide-type ring resonator 52 and light intensity detector 59 to detect an intensity of the probe light.

In non-invasive substance analysis apparatus 1f, through hole 13 through which excitation light 21 passes is provided in sample support plate 10. Therefore, excitation light 21 reaches sample 15 at a stronger light intensity, without being absorbed by sample support plate 10. The absorption heat of sample 15 increases. In addition, the absorption heat of sample 15 becomes less likely to escape in the thickness direction (the direction in which the first main surface (main surface 10a) and the second main surface (main surface 10b) face each other) of sample support plate 10. The temperature signal output from temperature sensor 50 during irradiation of sample 15 with excitation light 21 increases. Therefore, the substance in sample 15 or on the surface of sample 15 can be analyzed more accurately.

It should be understood that the first to sixth embodiments disclosed herein are illustrative and non-restrictive in every respect. At least two of the first to sixth embodiments disclosed herein may be combined unless they are inconsistent. The scope of the present disclosure is defined by the terms of the claims, rather than the description above, and is intended to include any modifications within the scope and meaning equivalent to the terms of the claims.

REFERENCE SIGNS LIST 1, 1b, 1c, 1d, 1e, 1f non-invasive substance analysis apparatus; 10 sample support plate; 10a, 10b main surface; 11 substrate; 12 sample placement region; 13 through hole; 13c central axis; 14 low-thermal-conductivity film; 15 sample; 20 excitation light source; 21 excitation light; 21b light irradiation region; 22 optical chopper; 23 beam splitter; 24 photodetector; 25, 26, 50 temperature sensor; 27 temperature sensor main body; 28 protective film; 30, 32 electrical wire; 34 lock-in amplifier; 35 multiplier; 36 low pass filter; 37 signal processing unit; 38 substance analysis unit; 40, 41 reference temperature sensor; 45 optical medium; 51 first optical waveguide; 51a, 51b end; 52 waveguide-type ring resonator; 53 second optical waveguide; 53a, 53b end; 54 clad layer; 55, 56 terminal portion; 58 probe light source; 59 light intensity detector.

The invention claimed is:

1. A non-invasive substance analysis apparatus comprising:
 a sample support plate having a first main surface including a sample placement region, and a second main surface opposite to the first main surface;
 an excitation light source to emit excitation light toward a sample placed on the sample placement region;
 at least one temperature sensor provided on the first main surface; and
 a reference temperature sensor provided on the first main surface, wherein
 a through hole extending from the sample placement region to the second main surface is provided in the sample support plate,
 the excitation light is applied to the sample through the through hole,
 the reference temperature sensor is provided in the sample placement region and comes into contact with the sample,
 in a plan view of the first main surface, a second distance between the reference temperature sensor and the through hole is ten times or more as long as a first distance between the at least one temperature sensor and the through hole, and
 the apparatus further comprises processing circuitry configured as a substance analysis unit to perform substance analysis on the sample based on detection values of the at least one temperature sensor and the reference temperature sensor.

2. The non-invasive substance analysis apparatus according to claim 1, wherein
 the at least one temperature sensor is provided in the sample placement region and comes into contact with the sample.

3. The non-invasive substance analysis apparatus according to claim 1, wherein the sample support plate includes a substrate and a low-thermal-conductivity film provided on the substrate and having a thermal conductivity lower than that of the substrate, at least a part of the first main surface is formed by the low-thermal-conductivity film, and the at least one temperature sensor is provided on the low-thermal-conductivity film.

4. The non-invasive substance analysis apparatus according to claim 1, further comprising a periodical intensity modulation unit that subjects the excitation light applied to the sample to periodical intensity modulation to generate a temperature variation signal of the at least one temperature sensor, wherein the substance analysis unit performs the substance analysis in the sample or on a surface of the sample based on the temperature variation signal of the at least one temperature sensor, and the temperature variation signal corresponds to a temperature variation of the sample measured by the at least one temperature sensor during analysis of the sample.

5. The non-invasive substance analysis apparatus according to claim 1, further comprising:

a signal processing circuit, wherein the at least one temperature sensor includes a plurality of temperature sensors, the signal processing circuit outputs an average of a plurality of temperature variation signals, each of the plurality of temperature variation signals corresponds to a temperature variation of the sample measured by a corresponding one of the plurality of temperature sensors during analysis of the sample, and the substance analysis unit performs the substance analysis in the sample or on a surface of the sample based on the average of the plurality of temperature variation signals.

6. The non-invasive substance analysis apparatus according to claim 1, further comprising:

a signal processing circuit, wherein the signal processing circuit calculates a calibrated temperature variation signal of the at least one temperature sensor by calibrating a temperature variation signal of the at least one temperature sensor with a reference temperature variation signal of the reference temperature sensor, the substance analysis unit performs the substance analysis in the sample or on a surface of the sample based on the calibrated temperature variation signal, the temperature variation signal corresponds to a temperature variation of the sample measured by the at least one temperature sensor during analysis of the sample, and the reference temperature variation signal corresponds to a temperature variation of the sample measured by the reference temperature sensor during analysis of the sample.

7. The non-invasive substance analysis apparatus according to claim 1, wherein the at least one temperature sensor includes a temperature sensor main body, and the temperature sensor main body is a thermocouple, a thermopile, a thermistor, or a diode.

8. The non-invasive substance analysis apparatus according to claim 7, wherein the at least one temperature sensor further includes a protective film that covers the temperature sensor main body.

9. A non-invasive substance analysis apparatus comprising:

a sample support plate having a first main surface including a sample placement region, and a second main surface opposite to the first main surface;

an excitation light source to emit excitation light toward a sample placed on the sample placement region; and at least one temperature sensor provided on the first main surface, wherein a through hole extending from the sample placement region to the second main surface is provided in the sample support plate, the excitation light is applied to the sample through the through hole, the apparatus further comprises processing circuitry configured as a substance analysis unit to perform substance analysis on the sample based on detection values of the at least one temperature sensor, and the at least one temperature sensor includes a first optical waveguide on which probe light is incident, a waveguide-type ring resonator optically coupled to the first optical waveguide, a second optical waveguide optically coupled to the waveguide-type ring resonator, from the second optical waveguide and a light intensity detector to detect an intensity of the probe light.

\* \* \* \* \*